(12) United States Patent
Rao et al.

(10) Patent No.: US 9,943,296 B2
(45) Date of Patent: Apr. 17, 2018

(54) SURGICAL METHOD AND CLAMPING APPARATUS FOR REPAIR OF A DEFECT IN A DURAL MEMBRANE OR A VASCULAR WALL, AND ANASTOMIC METHOD AND APPARATUS FOR A BODY LUMEN

(76) Inventors: Rob K. Rao, Hercules, CA (US); Mike Y. Chen, San Marino, CA (US)

( * ) Notice: Subject to any disclaimer, the term of this patent is extended or adjusted under 35 U.S.C. 154(b) by 2194 days.

(21) Appl. No.: 12/554,941

(22) Filed: Sep. 7, 2009

(65) Prior Publication Data
US 2010/0057115 A1    Mar. 4, 2010

Related U.S. Application Data

(63) Continuation-in-part of application No. 11/533,623, filed on Sep. 20, 2006, now abandoned.

(60) Provisional application No. 60/718,926, filed on Sep. 20, 2005.

(51) Int. Cl.
*A61B 17/00* (2006.01)
*A61B 17/11* (2006.01)

(52) U.S. Cl.
CPC .......... *A61B 17/0057* (2013.01); *A61B 17/11* (2013.01); *A61B 2017/00004* (2013.01); *A61B 2017/00575* (2013.01); *A61B 2017/00592* (2013.01); *A61B 2017/00597* (2013.01); *A61B 2017/00606* (2013.01); *A61B 2017/00619* (2013.01); *A61B 2017/00623* (2013.01); *A61B 2017/00867* (2013.01); *A61B 2017/1107* (2013.01); *A61B 2017/1135* (2013.01)

(58) Field of Classification Search
USPC ................ 606/151, 157, 213, 215, 216, 218
See application file for complete search history.

(56) References Cited

U.S. PATENT DOCUMENTS

| | | | |
|---|---|---|---|
| 3,874,388 A * | 4/1975 | King et al. | ..................... 606/232 |
| 4,744,364 A | 5/1988 | Kensey | |
| 4,852,568 A | 8/1989 | Kensey | |
| 4,890,612 A | 1/1990 | Kensey | |
| 5,053,046 A * | 10/1991 | Janese | ........................... 606/215 |
| 5,342,393 A | 8/1994 | Stack | |
| 5,350,399 A | 8/1994 | Erlebacher et al. | |
| 6,080,183 A | 6/2000 | Tsugita et al. | |
| 6,312,446 B1 | 11/2001 | Huebsch et al. | |
| 6,656,206 B2 * | 12/2003 | Corcoran et al. | ............. 606/213 |

(Continued)

OTHER PUBLICATIONS

Yuguchi et al "PTFE-fascia patch inlay method for the anterior approach for cervical intradural spinal lesion" Spinal Cord 40: 601-603 (2002) p. 601-602.

*Primary Examiner* — Alexander Orkin
(74) *Attorney, Agent, or Firm* — Blynn L. Shideler; Krisanne Shideler; BLK Law Group

(57) ABSTRACT

A surgical method and apparatus of repairing a tear, cut or defect in the body tissue, specifically the dura or vascular wall, is disclosed. An inner plate is placed on the tissue's inner surface in a position completely overlapping the tissue defect. An outer plate is placed on the tissue's outer surface in a position completely overlapping the defect and aligned with the inner plate. The inner and outer plates have perimeters larger than the perimeter of the defect and include coiled ribs. The inner plate is coupled to the outer plate such that the peripheral edges of the body tissue defect are securely clamped between the inner and outer plates to provide a watertight repair to the tissue defect.

16 Claims, 13 Drawing Sheets

(56) References Cited

U.S. PATENT DOCUMENTS

| | | |
|---|---|---|
| 6,790,218 B2 * | 9/2004 | Jayaraman .................... 606/191 |
| 6,962,591 B2 | 11/2005 | Lerch |
| 7,192,439 B2 | 3/2007 | Khairkhahan et al. |
| 7,361,178 B2 | 4/2008 | Hearn et al. |
| 2003/0100920 A1 | 5/2003 | Arkin et al. |
| 2004/0073242 A1 * | 4/2004 | Chanduszko ................. 606/157 |
| 2004/0133236 A1 * | 7/2004 | Chanduszko ................. 606/213 |
| 2005/0234509 A1 | 10/2005 | Widomski et al. |
| 2005/0251154 A1 | 11/2005 | Chandoszko et al. |
| 2006/0052821 A1 * | 3/2006 | Abbott et al. ................. 606/213 |
| 2006/0217763 A1 | 8/2006 | Abbott et al. |
| 2008/0243182 A1 * | 10/2008 | Bates et al. .................. 606/213 |
| 2009/0177225 A1 * | 7/2009 | Nunez et al. ................. 606/213 |
| 2009/0270911 A1 * | 10/2009 | Shipp ........................... 606/213 |

\* cited by examiner

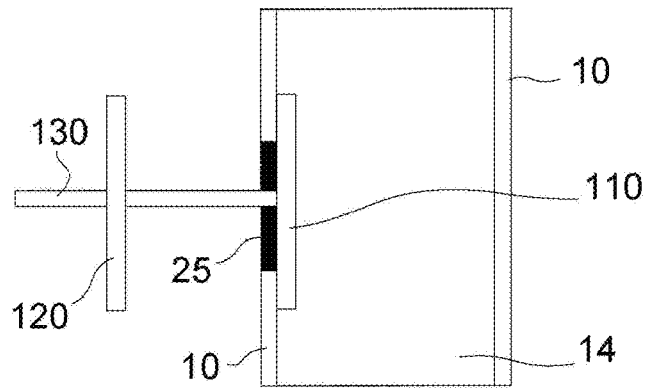
Fig. 7
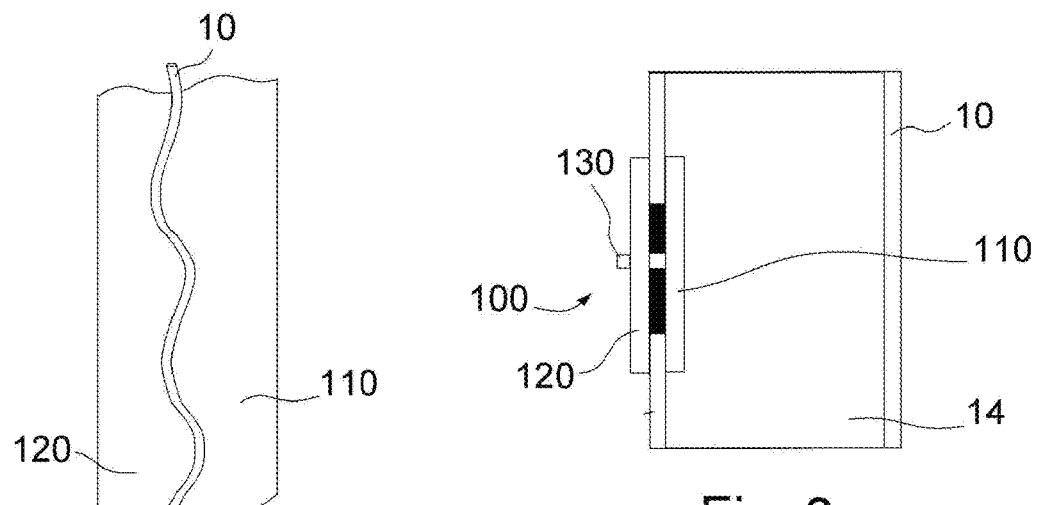
Fig. 9
Fig. 8

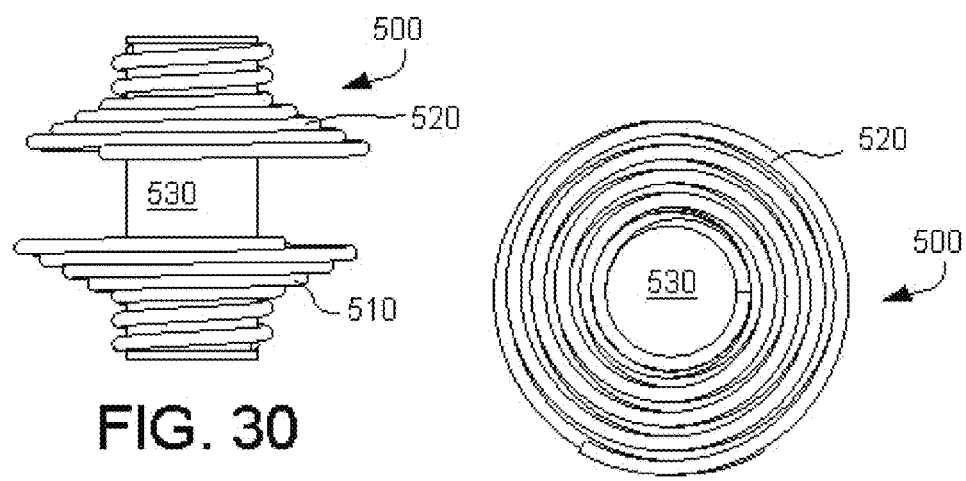
FIG. 30
FIG. 33
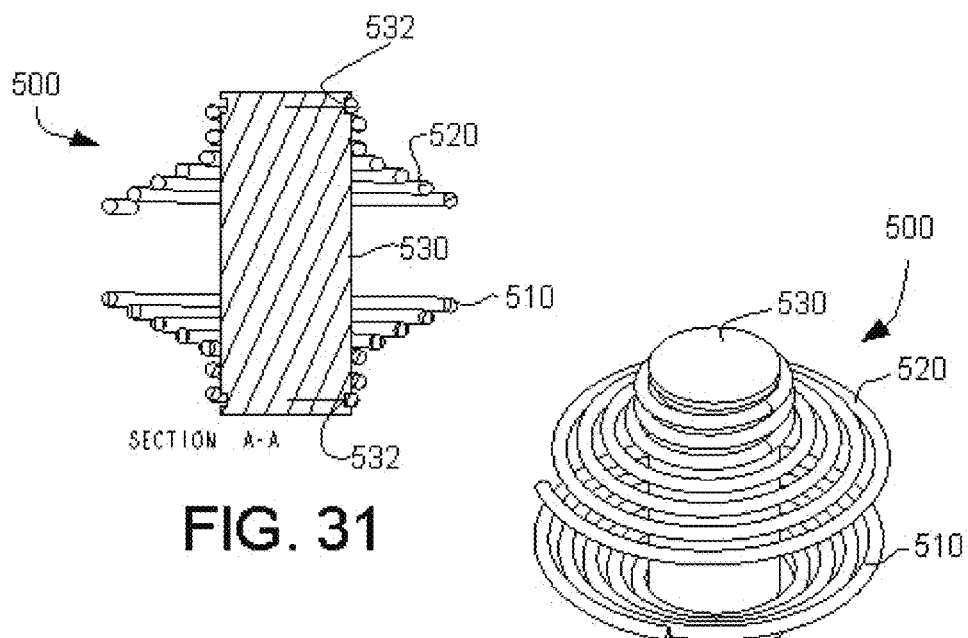
FIG. 31
FIG. 32

SURGICAL METHOD AND CLAMPING APPARATUS FOR REPAIR OF A DEFECT IN A DURAL MEMBRANE OR A VASCULAR WALL, AND ANASTOMIC METHOD AND APPARATUS FOR A BODY LUMEN

RELATED APPLICATIONS

The present application is a Continuation-in-part of U.S. patent application Ser. No. 11/533,623 filed Sep. 20, 2006 entitled "Surgical Method and Clamping Apparatus for Repair of a Defect in a Dural Membrane or a Vascular Wall, and Anastomic Method and Apparatus for a Body Lumen". U.S. patent application Ser. No. 11/533,623 claimed the benefit of Provisional Patent Application Ser. No. 60/718,926, filed Sep. 20, 2006 and entitled "Surgical Method and Clamping Apparatus for Repair of a Defect in a Dural Membrane or a Vascular Wall, and Anastomic Method and Apparatus for a Body Lumen". U.S. patent application Ser. No. 11/533,623 published as publication number 2007/0093860, which is incorporated herein by reference in its entirety

BACKGROUND OF THE INVENTION

1. Field of the Invention

The present invention relates to repair of a defect in the vascular wall for vascular surgery and to repair of a defect in the dural membrane for spinal and cranial surgery. More particularly the present invention relates to a surgical method and surgical clamping system for vascular repair and/or for dural membrane repair using opposed clamping plates having coiled ribs.

2. Background Information

Dural Membrane

The dura 10 (see FIG. 1), also called dural membrane and dura layer, is a layer of the membranous sac which covers the two parts of the central nervous system, the brain and spinal cord. A layer of fluid 12, termed cerebrospinal fluid, is present in the sub-arachnoid space between the dura and the structures of the central nervous system (i.e. the brain 14 or the spinal cord) and functions as a cushion as shown in FIG. 1. The other layers, the arachnoid layer 16 and pia layer 18, are very thin and structurally not significant for the purposes of the discussion in this application. The arachnoid layer 16 and the pia layer 18 are typically not specifically addressed in the repair of a rip, cut, rupture, tear, piercing or other defect in the dural membrane 10, in which a defect will generally also affect these structures. The term defect is used generically herein to reference all discontinuities in the membrane surface, including cuts, tears, naturally forming defects, rips, ruptures, piercing, or other break in the membrane surface.

The dura 10 is often damaged during surgery and requires repair so that cerebrospinal fluid 12 remains contained. A cerebrospinal fluid leak places the patient at substantial risk for meningitis (infection surrounding the brain), and generally causes a severe headache since the brain 14 sags without the supportive function of the fluid 12. The dura 10 is damaged purposefully (e.g. cut), on occasion, so that surgeons can access the underlying spinal cord or brain 14. Other times, the dura 10 is inadvertently injured during the course of spine surgery where access to the spinal cord is not required, i.e. removal of a herniated disc. The rate of inadvertent spinal fluid leaks due to dural membrane damage occurs in about 5% of open spinal procedures.

The numerous dural membrane repair methods can be generally categorized into: (a) those that re-approximate the edges of the defect (i.e. sutures or staples), (b) those that seal the defect with some type of glue, and (c) lastly, those that place a patch over the defect. Oftentimes, a combination of these strategies is used; however, significant drawbacks, which will be detailed further, are associated with each of these methods.

The first category of techniques, re-approximation of the edges, is the current method of choice and is represented in FIGS. 2a and 2b. Most commonly, fine suture 20, such as 4-0 silk available from US Surgical or 5-0 prolene available from Ethicon, is used to repair the dural defect. The suturing method is highly effective, but it is often not an option because of problems with either visualizing the dural membrane defect or with having enough room in the incision to manipulate the needle driver at the proper angle. Visualization of the defect 25 in the dura 10 can be difficult because the spine is often approached from the posterior (back) during surgery, as represented in FIG. 3, but the defect may occur in the anterior aspect (front) of the thecal sac. The spine 22, in FIG. 3, is being viewed behind and slightly off to the left of the patient. One analogy used to explain this relationship of elements is that the spine 22 is like a tunnel and the dural tube 10 is like a long worm going through it. The roof of the spinal canal is dissected away in FIG. 3 exposing the back and left side of the dural tube 10. Typical surgical exposure is rarely as good as shown in FIG. 3. The front and the sides of the dural tube 10 are essentially inaccessible to suturing instruments when the approach is from the posterior (back). Moreover, the back (side facing the surgeon) of the dural tube 10 is also extremely difficult to suture especially when the exposure is limited, as in microsurgery spine cases particularly when minimally invasive techniques such as endoscopes or tubes are used.

In an effort to provide surgeons with a tool that could compensate for the shortcomings of the suturing technique, titanium dural staplers, such as US Surgical's Auto Suture VCS™ disposable clip applier, were developed. These staplers possess the advantage of being able to work in tighter spaces; however, effective application is technically difficult for a number of reasons. One such reason is that these staplers are bulky and impede visualization of the affected area. Another frustrating problem is that the staples are difficult to place accurately, and to make matters worse, the staples have a known tendency to slip off.

The second major strategy for the repair of dural defects is the use of glues which are also referred to as tissue sealants. These glues are gelatinous masses that cover the defect, but do not actually glue the edges of the dura 10 together. Most of the approved biological sealants work through the basis of creating a fibrin mesh. When used by themselves, glues such as Tisseal™, are associated with significant drawbacks. One potential shortcoming is that tissue sealants require dry conditions to set; however, the spinal fluid leak is by definition a wet condition thus precluding use. Another concern is that the adhesive and tensile strength of the formed gels are lacking. Fluids tend to leak around the gelatinous mass, which is not firmly attached to the dura, or dissect through it. Because of these limitations, tissue sealants are commonly used as a supplement to other dural membrane closure techniques.

The third major tactic for repairing cerebrospinal fluids leaks is the use of a graft to patch over the defect. Several types of patches are available ranging from those harvested from the patient to those of the synthetic variety. The handling characteristics of these grafts vary widely and as such each type will be individually discussed.

Harvested grafts include those consisting of fat and muscle. If possible these patches are placed into the defect as a plug; otherwise, they are used like a blanket to cover the dural membrane defect, such as represented in FIG. 4. Sometimes the fat or muscle is secured to the dura 10 with stitches. Overall, these natural patches are effective and are used especially in cases where the spinal fluid leak is difficult to stop. The main drawbacks, however, are that significant additional tissue trauma is incurred with the act of harvesting, and that achieving a secure "plug" is not easy.

One alternative to fat and muscle grafts is bovine pericardium such sold under the brand name Duraguard™ by Synovis. In using animal tissues, the patient is spared the additional trauma of harvesting. However, since pericardium possesses no inherent stickiness to dura 10, it is a patch that must be sutured in water tight fashion into the defect. While it is often used to repair extremely large dural membrane defects for brain surgery, the need to suture the perimeter of the Duraguard™ patch to the free edges of dura 10 essentially precludes the use of this technique in the spine. Patches made of synthetic collagen matrices represent an additional option that is commonly employed. The difference between these patches, such as sold under the brand Duragen™ sold by Integra, and the bovine pericardium patches is that they possess some inherent stickiness to the dura 10 that allows the Duragen™ patches to be placed over the defect and secured without the use of sutures. This feature allows for more ready utility in the spine procedures. However, without sutures, the seal is tentative, and is usually reinforced with a tissue sealant. Even this combination of the patch and tissue sealant is far from secure. As with the previously described methods, patients often have an extended hospital stay, remaining flat in bed for 3 to 5 days, to allow for healing so that the dura 10 is sealed. This form of graft is particularly effective for fixing dural membrane leaks that are difficult to visualize. A competing patch type dural membrane repair product is manufactured by Codman.

By using a combination of current dural membrane repair techniques, most dural membrane defects can be fixed. The drawbacks either relate to technical difficulty, additional patient suffering and cost, or lack of certainty. It will be difficult to improve the dural repair methods that exist currently through improvements in the specifics of these techniques alone. Advancements in suture and staple technology will have to overcome the fact that a suture/staple line will always be more prone to leaks than a solid seal, and will also be more time consuming. Though a large amount of sealant technology research is being performed, there is considerable difficulty in finding glues that will attach to wet surfaces and remain biocompatible at the same time. Graft technology, such as Duragen™ brand grafts, will also require a substantial leap to overcome the lack of adherence to dural membrane edges. However, they will continue to serve a function particularly when the dural membrane defect cannot be easily visualized.

As spine surgery progresses more and more from traditional large open incisions to minimally invasive surgery, the limitations of current dural membrane closure techniques have become more apparent since the mainstay, the traditional suturing techniques, become even more difficult to perform If a new device could safely, effectively and rapidly close dural tears, then the current techniques could be readily supplanted as well as adding to the armentarium of tools for true minimally invasive procedures. In our opinion, there is a growing need for effective and efficient surgical methods and apparatus for the repair of defects in the dural membrane.

Blood Vessels Trauma

Similar to the dural tube, blood vessels also possess a lumen. Blood vessels in the body are of two types, arteries that carry blood from the heart to other organs and veins that carry blood from the body back to the heart and lungs so that re-oxygenation can occur. Blood in arteries is under high pressure, and as a result, arteries have a relatively thick wall which can be comparable to that of the dura. The diameter of arteries varies considerably from millimeters to about 3 centimeters (the aorta). The pressure in veins is low, and as a result, the walls are very thin.

Blood vessels are often injured from trauma or inadvertently during surgery. Repair of blood vessels is performed in the fields of trauma surgery, transplant surgery, neurosurgery, cardio-thoracic surgery, vascular surgery, orthopedic surgery, and general surgery. Failure to repair damaged blood vessels can lead to death by exsanguination, stroke, venous insufficiency, and loss of an organ or limb.

When blood vessels are damaged, surgeons most often will elect to sacrifice the vessel using methods such as suture ligation, vascular clips, and electrocauterization. Removing the artery or vein from circulation is extremely effective in addressing blood loss, but a poor option if the damaged blood vessel has an important function. For example, obviously grave consequences would occur if the aorta, the main artery of the body, was ligated.

Several techniques can be used to repair damaged blood vessels while preserving them at the same time. One common method is the application of a thrombin soaked sponge or a hemostatic gel to the bleeding vessel. These devices cause a clot to form and are very effective at stopping low pressure and low flow bleeding. The limitation of this method is that vigorous bleeding cannot be easily controlled. Numerous companies (Tisseal, Surgifoam, Surgicel, Avitene, Fibrillar, Flowseal) make commercial versions of this device.

Another hemostasis technique is the use of suture to close the defect in the blood vessel. The success of this method varies according to the surgical exposure, size and type of blood vessel. Large arteries and veins can be sutured under optimal conditions. However, placing these sutures is time consuming and often causes critical narrowing the vessels which could lead to inadequate circulation.

A third option is the use of electro-cautery techniques to close the defect. In this method a device such as the bipolar or electrosurgical pencil causes the tissue surrounding the defect to shrink and hopefully close the gap. Only very small defects with low flow bleeding can be treated with this technique and the risk of damaging the normal portions of the affected blood vessel is substantial.

One final alternative to closure of defects in blood vessels is the use of a patch. These patches can be natural (i.e. saphenous vein graft) or synthetic (Dacron® or polytetrafluroethylene (PTFE-Goretex®). Furthermore, they exist in different configurations such as a flat patch or in the form of a tube. Their use as a device to close vessel wall defects is limited for several reasons. First and foremost is the technical difficulty of sewing in these grafts particularly when time is of the essence and exposure is less than optimal as occurs in a emergency situations. Second, placement of these grafts necessitates a large surgical exposure which may not exist. Lastly, many of these grafts do not exhibit long term patency.

Taken together, the current the above described commercial methods for repair of damaged blood vessels possess limitations similar to those associated with existing methods of dural membrane repair. There is a need for effective and efficient surgical methods and apparatus for the repair of defects in vascular walls.

Blood Vessel Surgical Puncture

It a related but slightly different vascular repair field is the repair of the intentional damage or defect in a blood vessel. Numerous medical procedures are performed which require formation of a puncture or the like in a blood vessel for the introduction of various devices, such as catheters. Access to arterial and venous vascular systems is necessary for both diagnostic and therapeutic medical procedures. For example, diagnostic arteriography is a radiologic procedure which permits visualization of the arterial system for the diagnosis of disease in various organ systems. Some frequent applications are cardiac catheterization, peripheral vascular angiography, mesenteric angiography, and cerebral angiography. Therapeutic trans-arterial procedures, such as percutaneous transluminal coronary angioplasty, have expanded the use of arterial access even further. All these representative techniques involve cannulation of an artery so that a catheter may be inserted and advanced into the arterial system.

The femoral artery at the junction of the thigh and the abdomen is the most frequent arterial puncture site, but the carotid artery in the neck, the brachial artery in the mid-arm, and the axillary artery are also used. A percutaneous sheath is usually used whenever multiple catheters are used. When the sheath is removed, the remaining 1.5 to 5.0 millimeter hole in the artery would spurt blood with significant blood loss unless certain measures are taken. Effective arterial puncture sealant devices have been proposed, such as described in U.S. Pat. Nos. 4,744,364; 4,852,568 and 4,890,612, for the mechanical sealing of-such punctures. In such cases, a sealing device in the form of an expandable closure member is to be inserted through a puncture in the vessel, expanded while within the vessel and then retracted against and through the puncture by means of a retraction filament. Thereafter, the filament is left extending from the site of the puncture and through the skin of the patient while being secured in position on the skin of the patient as by a strip of conventional tape. However, such devices permit the exposed thread to be a site for infection. Further, anchorage of the enclosed member in place by a thread which passes through the skin of a patient may not be reliable so that bleeding may occur by accidental displacement of the sealant device. Further, displacement of the sealant device into the artery would result in arterial occlusion and gangrene.

U.S. Pat. No. 5,350,399 proffered a somewhat better solution for sealing a puncture wound in the form of sealing device is composed of an intra-arterial occluder and an extra-arterial occluder, both made of resilient biocompatible and/or bioabsorbable material and held in place via a saw-toothed guide extending integrally from the intra-arterial occluder. However the clamping configuration proposed in this patent is not optimal for other vessel defects outside of the well defines small puncture wound. Improvements can be made to the inner occluder and outer occluder and the guide there between to make this type of clamping vessel repair solution more effective and more practical to a wider variety of vessel repair applications.

SUMMARY OF THE INVENTION

The concept behind the present invention addressing at least some of the above issues and relating to the repair of a defect in dural membrane or vascular wall is simply to trap the edges of the defect in the dura or vascular wall using two plates secured to one another which securely trap the edges of the defect between the plates.

A surgical method of and apparatus for repairing a defect in the dura according a non-limiting embodiment of the present invention includes placing an inner plate on an inner surface of the defect in the dura in a position overlapping the defect in the dura, whereby the inner plate has a perimeter in plan view larger than the perimeter in plan view of the defect in the dura. An outer plate is placed on an outer surface of the defect in the dura in a position completely overlapping the defect in the dura and aligned with the inner plate, whereby the outer plate has a perimeter in plan view larger than the perimeter in plan view of the defect in the dura. The inner plate is coupled to the outer plate such that the peripheral edges of the defect in the dura is securely clamped between the inner and outer plates to provide a watertight repair to the defect in the dura.

A surgical method of and apparatus for repairing a defect in a vascular wall according a non-limiting embodiment of the present invention includes placing an inner plate on an inner surface of the defect in the vascular wall in a position completely overlapping the defect in the vascular wall, whereby the inner plate has a perimeter in plan view larger than the perimeter in plan view of the defect in the vascular wall. An outer plate is placed on an outer surface of the defect in the vascular wall in a position completely overlapping the defect in the vascular wall and aligned with the inner plate, whereby the outer plate has a perimeter in plan view larger than the perimeter in plan view of the defect in the vascular wall. The inner plate is coupled to the outer plate such that the peripheral edges of the defect in the vascular wall is securely clamped between the inner and outer plates to provide a watertight repair to the defect in the vascular wall.

These and other advantages of the present invention will be clarified from the attached figures wherein like reference numerals represent like elements throughout.

BRIEF DESCRIPTION OF THE FIGURES

FIG. 7 is a schematic view of the inner plate of FIG. 5 in a position adjacent the dural defect and an outer plate of the clamping apparatus according to one aspect of the present invention being moved into position;

FIG. 8 is a schematic view of the clamping apparatus of FIG. 7 in a final dural membrane repairing position;

FIG. 9 schematically illustrates interlocking surface ridges for the inner and outer plates of the clamping apparatus according to one embodiment of the present invention;

FIG. 30 is a schematic elevation side view of a clamping apparatus according to another embodiment of the present invention;

FIG. 31 is a schematic sectional side view of the clamping apparatus according to FIG. 30;

FIG. 32 is a schematic perspective view of the clamping apparatus according to FIG. 30; and FIG. 33 is a schematic top plan view of the clamping apparatus according to FIG. 30.

DESCRIPTION OF THE PREFERRED EMBODIMENT

Figure 1:
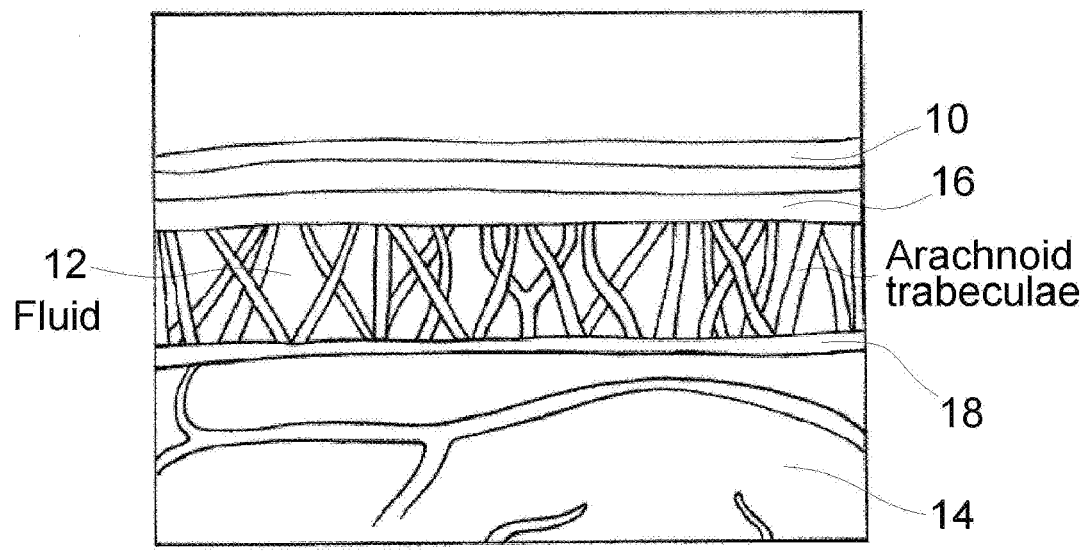
FIG. 1 is a schematic drawing of the different membranes covering the brain.
Figure 2A:
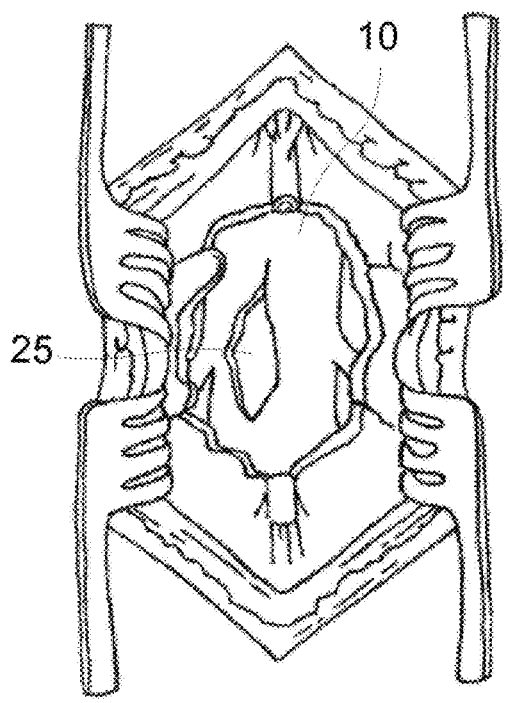
FIGS. 2a and 2b are schematic drawings depicting a dural membrane defect and closure of the defect with sutures, respectively.
Figure 2B:
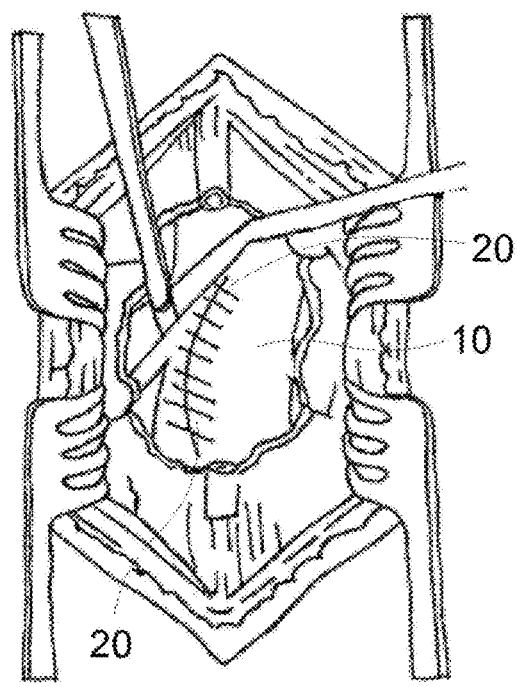
Figure 3:
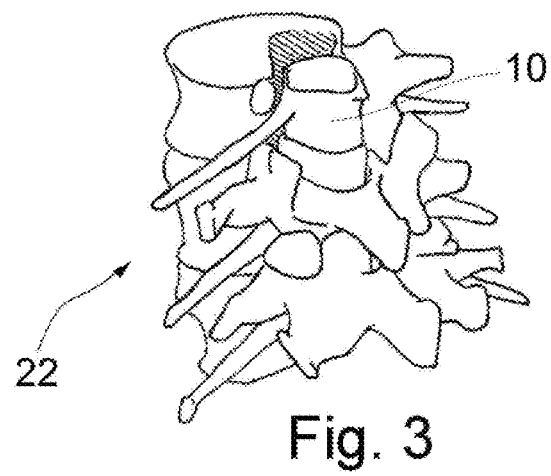
FIG. 3 is a schematic anatomical representation of the spine from a posterior approach.
Figure 4:
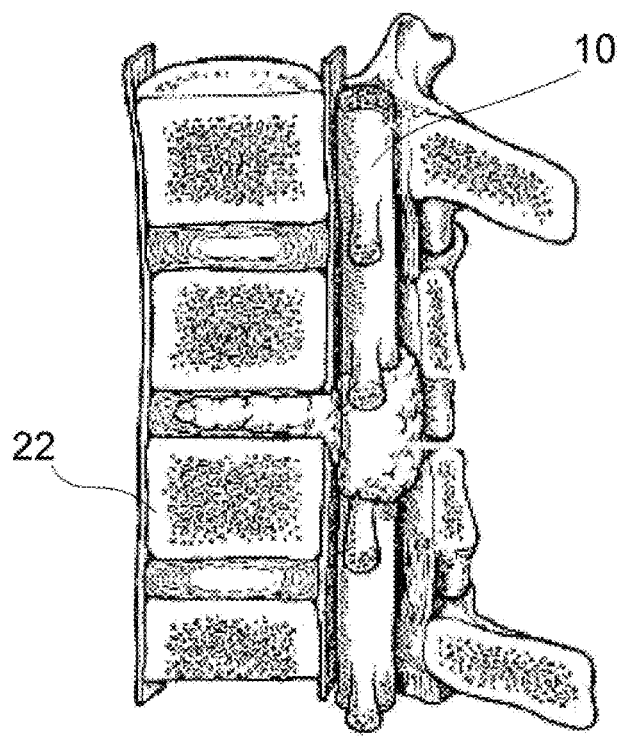
FIG. 4 is a schematic of a natural tissue graft used to close a dural tube defect to seal a cerebrospinal fluid leak.

As noted above in the summary, the concept behind a dural defect surgical clamping apparatus 100 of the present invention is simply to trap the edges of the defect 25 in the dura 10 using two plates 110, 120 secured to one another. The plates, as referenced in this application, can also be referenced as interior and exterior occluders, respectively. The components of the clamping apparatus 100 include an inner plate 110 that is positioned on the inside of the dura 10 (through the defect 25 to be sealed), an outer plate 120 opposed to the inner plate 110 and a coupler 130 to secure the two plates 110 and 120 together to clamp the dura 10 therebetween.

Possible materials for the plates 110 and 120 include: poly-ethyl-ethyl-ketone (PEEK), high molecular weight poly-ethylene, silastic, titanium alloys, polypropelene, poly-glycolic acid, and poly-lactic acid. The latter two materials are bio-absorbable, more precisely bio-resorbable, and can be reinforced with carbon fiber. The term "biodegradable" refers to a biological mediated degradation process such as enzymatic and/or cellular processes. "Bioresorption" refers to a chemically mediated degradation process such as hydrolysis where the degradation products are then incorporated into normal metabolic pathways like the Krebs Cycle. "Bioabsorbable" technically also refers to a chemically mediated degradation, but the degradation products are generally excreted through one of the body's organ systems. All three terms are unfortunately used indiscriminately in both scientific and clinical literature and this has caused significant confusion. Within the meaning of this application "bioabsorbable" will be used in its broadest sense in the art and will therefore generically reference materials that are biodegradable, bio-resorbable or bio-absorbable in accordance with the above definitions.

Figure 5:
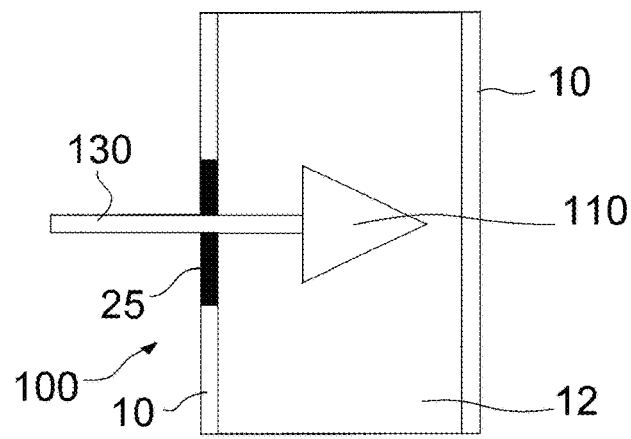
FIG. 5 is a schematic view of the insertion step of a retracted inner plate of a dural membrane clamping apparatus according to one embodiment of the present invention through a dural defect to be sealed.
Figure 6:
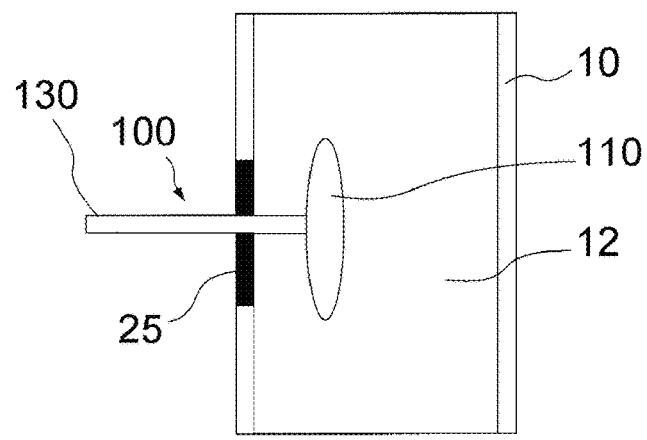
FIG. 6 is a schematic view of a deployment of the inner plate of FIG. 5.

In one aspect of the present invention the inner plate 110 may be moved to a retracted insertion position to aid in placement beneath the dura 10. The inner plate 110 may also be a circular plate in plan view, although any shape of plate could be used. A circular shape for the interior plate 110 does provide symmetrical advantages. Depending on the size and shape of the defect as well as the presence of sensitive underlying neurological structures, the inner plate 110 can be inserted in the closed un-deployed position as shown in FIG. 5 or in the open fully deployed position, if possible. Following the insertion of the retracted un-deployed position of the inner plate 110, the retracted inner plate 110 can then open and fully deploy as the inner plate 110 as shown in FIG. 6. This deployment step also adds greater safety by allowing errant nerves, and other tissue, to be pushed out of the way during the opening of the inner plate 110, preventing the clamping of unwanted tissue between the two plates 110 and 120 when finally installed. These nerves are occasionally inadvertently trapped by staples or sutures in prior art methods.

The retraction and deployment mechanism may be through any appropriate mechanism. For example, the material forming the inner plate 110 may be flexed to the retracted position and held there against the elastic biasing force of the material forming the inner plate 110 by a separate holding member, such as sheath 112 of FIGS.

16-17, and when the holding member releases the contracted inner plate 110, the inner plate 110 returns to the fully deployed open position through the restoring force in the material itself. Another alternative is to have shape memory alloy strips (not shown), such as nitinol or titanium, incorporated into the inner plate 110, wherein in one possible configuration is formed as ribs like in an umbrella, and which are by default in a curved retracted position and then manipulated into the deployed position. In other words, the radial individual nitinol strips move from a tight "U" shape in the un-deployed retracted position to a straight shape in the deployed position. Other contracting and expanding devices may be used to contract and expand or deploy the inner plate 110.

Following the positioning of the inner plate 110 in the interior of the dura 10, and deploying the inner plate 110 if it was inserted in a contracted position, the inner plate 110 is then brought into contact with the inner aspect of the dural defect as shown in FIG. 7. The matching outer plate 120 is then pushed down the coupler 130, or device stem, to lock with the inner plate 120 as shown in FIG. 8. It is important for the outer plate 120 and the inner plate 110 to generally align and it is important that the inner plate 110 and the outer plate 120 have a plane view larger than the periphery of the defect 25. A matching circular shape for the inner and outer plates 110 and 120 avoid alignment concerns. The circular profile for the inner and outer plates 110 and 120 allow the coupler 130 to include a threaded shaft portion 133 (shown in FIG. 13) engaging threads (not shown) on the outer plate 120, with the engaging threads allowing for sufficient clamping force to be created directly between the plates 110 and 120 in the final locked position to clamp against the tissue. A locking washer or clip (not shown) could be used to prevent the outer plate 120 from backing off of the threaded shaft portion 133 (if threads are used on the coupler 130). The excess portion of the coupler 130, i.e. the portion of the shaft extending beyond the outer plate 130 (and any retaining clip) may be removed following installation. This installation clamping process traps the edges of the defect 25 in the dura between the aligned plates 110 and 120, essentially placing a "manhole" cover over the defect 25. The faces of the plates 110 and 120 may further include meshing ridges and grooves as shown in FIG. 9 to further improve the seal around the defect 25. Further, a ratchet type stem could be used as one of many of the possible alternatives for the design of the coupler 130.

Other alternatives for the coupler configuration include use of adhesive material on the facing portions of the plates 110 and 120 to couple the inner and outer plates 110 and 120 together. The coupler 130 may include the use of a stem member as shown, primarily as a guide, and adhesives to provide the coupling compressive force between the plates.

Figure 10:
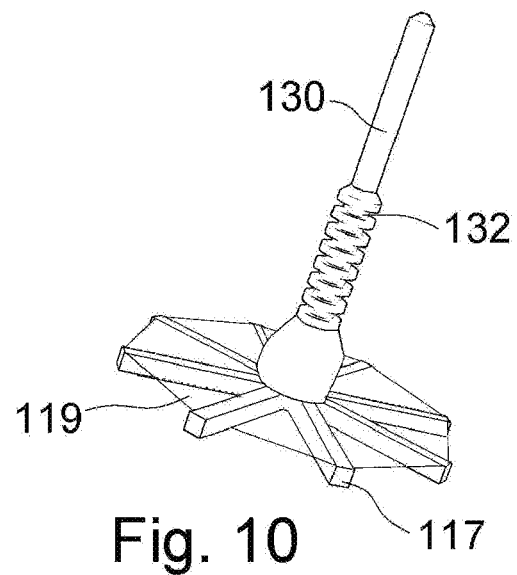
FIG. 10 is a perspective schematic view of an expanding inner plate and an integral locking stem coupling configuration for securing the inner and outer plates of the clamping apparatus according to one embodiment of the present invention.
Figure 11:
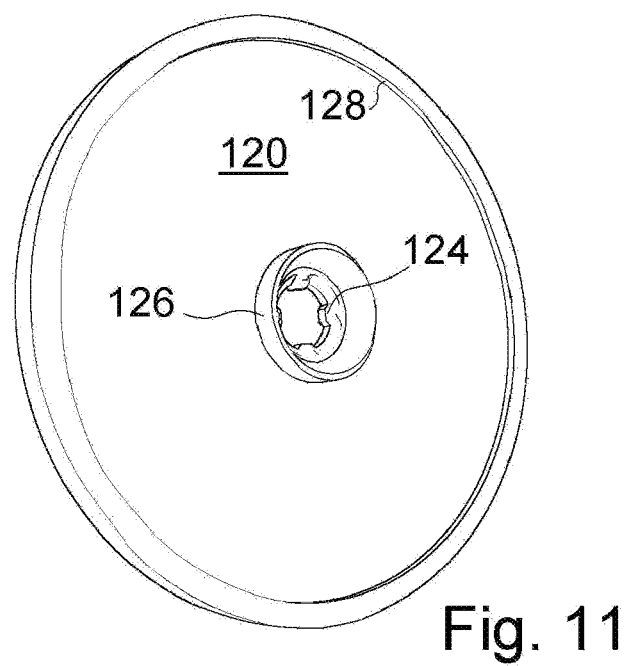
FIG. 11 is a perspective view of an outer plate configured to couple with the inner plate and stem of FIG. 10.

FIG. 10 is a perspective schematic view of an expanding inner plate 110 and an integral locking stem coupler 130 according to one embodiment of the present invention. The inner plate is formed of ribs 117 and flexible webbing 119 that easily allows for easy retraction to the contracted position shown in FIG. 5 above. The coupler 130 includes notches 132. FIG. 11 is a perspective view of an outer plate 120 configured to couple with the inner plate 110 and coupler 130 of FIG. 10. Specifically the plate includes flexible locking tabs 124 that engage within the notches 132. The tabs 124 are flexible enough to allow the plate 120 to be pushed down the stem of the coupler 130, with a beveled edge to allow the one-way movement. The plate may further include an alignment ring 126 on the inner side to assist in alignment with the inner plate 110. The outer plate 120 may be formed larger than the inner plate 110 with an outer retaining ring 128 as shown.

Figure 12A:
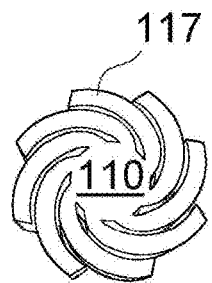
FIGS. 12a-d are schematic views of an expanding inner plate and an integral locking stem coupling configuration for securing the inner and outer plates of the clamping apparatus according to another embodiment of the present invention.
Figure 12B:
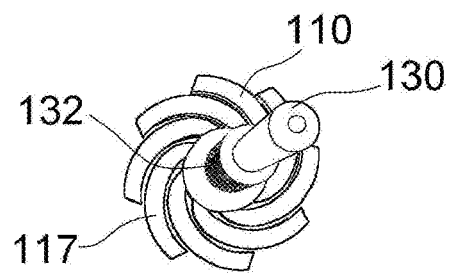
Figure 12C:
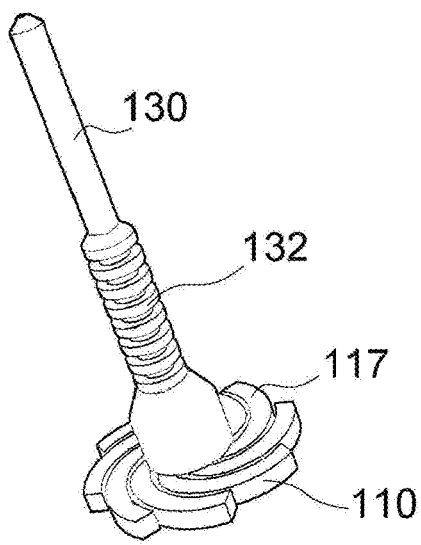
Figure 12D:
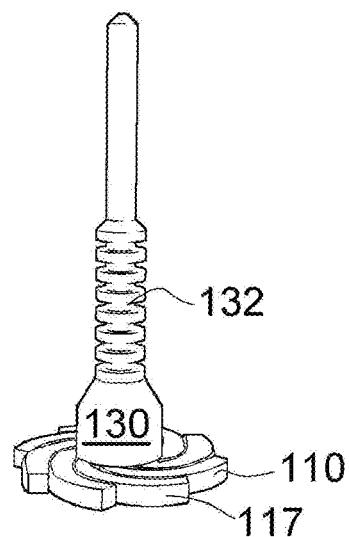

FIGS. 12a-d are schematic views of an expanding inner plate 110 and an integral locking stem coupler 130 as described above in FIG. 10, except that the ribs 117 are formed in a coil configuration. As best shown in FIG. 12a, in this embodiment the ribs 117 have a first end fixedly secured to the coupler 130 and a remote distal end extending away from the first end in a coil form. In this embodiment, the plate 110 includes a plurality of coil fibs 117 extending from the coupler 130.

Figure 13:
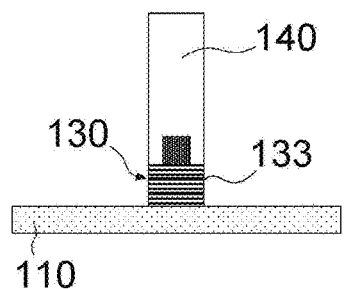
FIG. 13 is a schematic view of an inner plate and an integral locking stem and separable handle coupling configuration for securing the inner and outer plates of the clamping apparatus according to another embodiment of the present invention.
Figure 14:
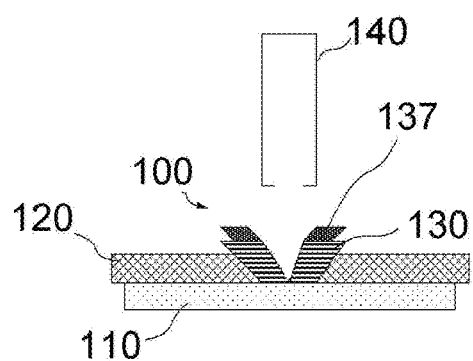
FIG. 14 is a schematic view of an inner plate and an integral locking stem and separable handle coupling configuration for securing the inner and outer plates of the clamping apparatus according to another embodiment of the present invention.

FIG. 13 is a schematic view of an inner plate 110 and an integral locking stem coupler 130 (with threaded portion 113) and separable handle 140 according to another embodiment of the present invention. This embodiment of the apparatus 100 a separable handle 140 allows for easy deployment of the inner plate 110, without separate trimming of excess stem portion. Any number of releasable connections between the separable handle 140 and the stem of the coupler 130 can be used. FIG. 14 is a schematic view of an inner plate 110 and an integral locking coupler 130 and separable handle 140 configuration according to another embodiment of the present invention. In this embodiment the coupler 130 is split and after the outer plate 120 is moved into position the handle 140 is removed and the split coupler 130 is spread apart as shown to lock the components together. A coupler handle 137 may be used to open the halves of the split coupler 130. This embodiment could be used with other coupling techniques such as threads.

Figure 15:
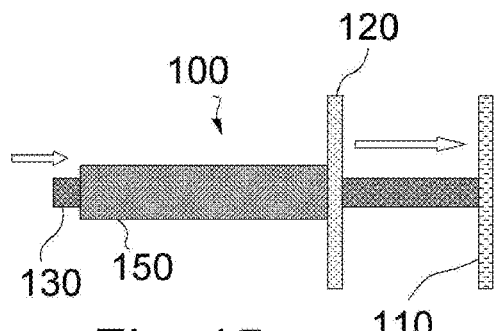
FIG. 15 is a schematic view of a clamping apparatus and separable outer plate pusher configuration according to another embodiment of the present invention.

FIG. 15 is a schematic view of a clamping apparatus 100 together with a separable outer plate pusher 150 according to another embodiment of the present invention. The outer plate pusher 150 is simply a mechanism to allow for remote attachment of the outer plate 120. The outer plate pusher 150 is separate from the outer plate 120 and will be removed, with excess stem of the coupler 130 if a separate handle 140 is not utilized, after installation.

Figure 16:
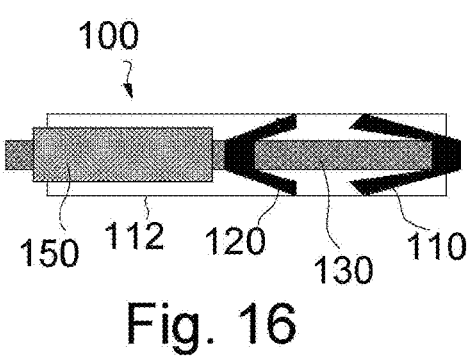
FIG. 16 is a schematic view of a clamping apparatus and separable outer plate pusher configuration with retracted inner and outer plates and outer sheath according to another embodiment of the present invention.
Figure 17:
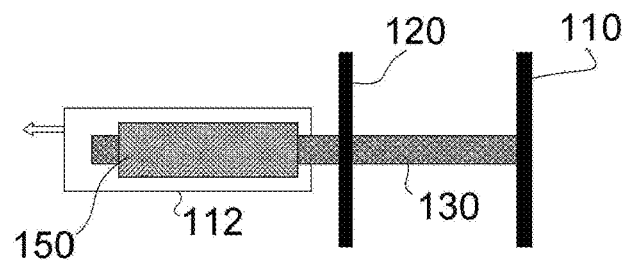
FIG. 17 is a schematic view of the clamping apparatus of FIG. 16 with the plates in a deployed position.

FIG. 16 is a schematic view of a clamping apparatus 100 with separable outer plate pusher 150, further including a plate holding sheath 112 as discussed above. In this configuration the inner plate 110 and the outer plate 120 are retractable. The retracted inner and outer plates 110 and 120 and outer sheath 112 according to this embodiment of the present invention allows for minimally invasive applications of the apparatus 100. FIG. 17 is a schematic view of the clamping apparatus 100 of FIG. 16 with the plates 110 and 120 in a deployed position, and it will be clear that the inner plate 110 will likely be deployed on the inside surface of the dural membrane 10.

Figure 24:
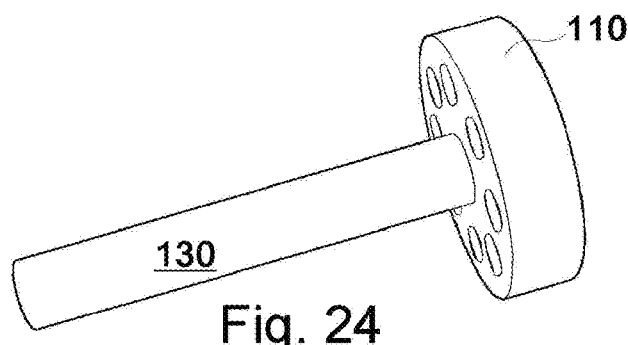
FIG. 24 is a schematic perspective view of an inner plate and an integral locking stem configuration of the clamping apparatus according to another embodiment of the present invention.
Figure 25:
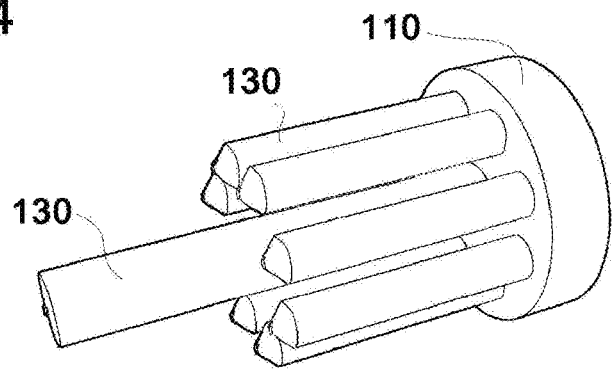
FIG. 25 is a schematic perspective view of an inner plate and an integral locking stem configuration of the clamping apparatus according to another embodiment of the present invention.
Figure 26:
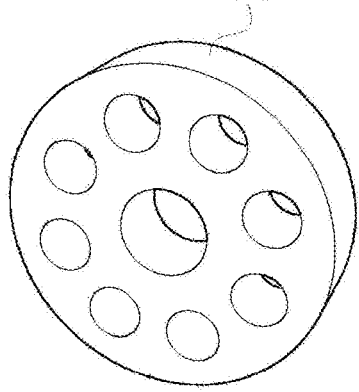
FIG. 26 is a schematic perspective view of an outer plate of the clamping apparatus using the inner plates of FIGS. 24-25.
Figure 27:
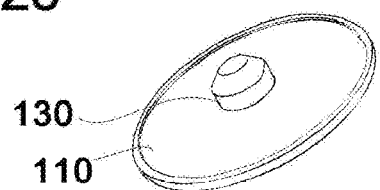
FIG. 27 is a schematic perspective view of an inner plate and an integral locking stem configuration of the clamping apparatus according to another embodiment of the present invention.
Figure 28:
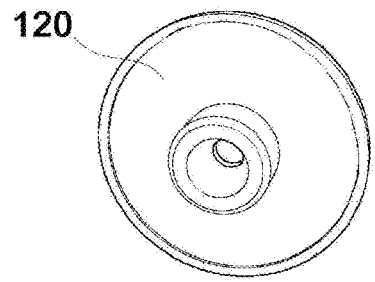
FIG. 28 is a schematic perspective view of an outer plate of the clamping apparatus using the inner plates of FIG. 27.

FIGS. 24-26 illustrate further embodiments of the apparatus 100 according to the invention. FIG. 24 is a schematic perspective view of an inner plate 110 and an integral locking stem 130, wherein the plate 110 includes one or more recesses therein. Where adhesive or the like is used to secure the plates 110 and 120, the recesses themselves will not detrimentally affect dura defect sealing. FIG. 25 is a schematic perspective view of an inner plate 110 and an integral locking stem(s) 130 configuration in a plurality of locking stems are provided. FIG. 26 is a schematic perspective view of an outer plate 120 of the clamping apparatus that will correspond to using the inner plates 110 of FIGS. 24-25;

FIGS. 27-28 illustrate a further embodiment of the apparatus 100 according to the invention. FIG. 27 is a schematic perspective view of an inner plate 110 and an integral locking stem configuration 130 of the clamping apparatus 100 and FIG. 28 is a schematic perspective view of an outer plate 120 of the clamping apparatus 100 using the inner plates of FIG. 27.

Figure 29:
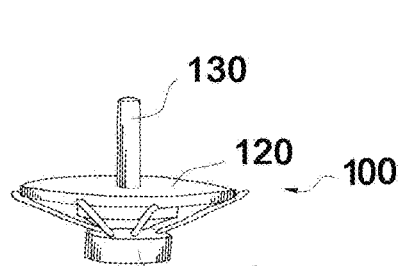
FIG. 29 is a photograph of a prototype depicting one of the possible mechanisms for deployment of the inner plate.

FIG. 29 is a photograph of a prototype of the apparatus 100 according to the invention depicting one of the possible mechanisms for outward sweeping deployment of the inner plate 120 described above.

Figure 18:
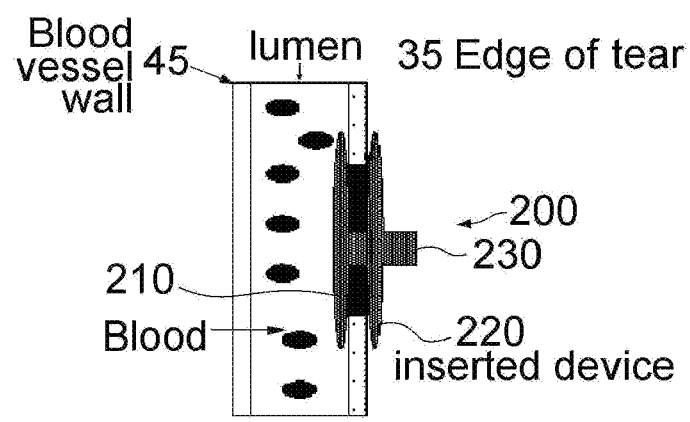
FIG. 18 is a schematic view of a vascular wall defect clamping mechanism according to one embodiment of the present invention.

The present invention discloses a surgical apparatus 200 and associated method for repairing a defect 35 in a vascular wall 45 according a non-limiting embodiment of the present invention as shown in FIG. 18. This method includes placing an inner plate 210 on an inner surface of the defect 35 in the vascular wall 45 in a position completely overlapping the defect 35 in the vascular wall 45, whereby the inner plate 210 has a perimeter in plan view larger than the perimeter in plan view of the defect 35 in the vascular wall 45. An outer plate 220 is placed on an outer surface of the defect 35 in the vascular wall 45 in a position completely overlapping the defect 35 in the vascular wall 45 and aligned with the inner plate 45, whereby the outer plate 220 has a perimeter in plan view larger than the perimeter in plan view of the defect 35 in the vascular wall 45. The inner plate 210 is coupled to the outer plate 220 through a coupler 230 such that the peripheral edges of the defect 35 in the vascular wall 45 are securely clamped between the inner and outer plates 210 and 220 to provide a watertight repair to the defect 35 in the vascular wall 45.

The inner plate 210 may be formed in the manner discussed above in connection with the inner plate 110 and is analogous thereto. The outer plate 220 may be formed in the manner discussed above in connection with the outer plate 120 and is analogous thereto. Further, the coupler 230 may be formed in the manner discussed above in connection with the coupler 130 and is analogous thereto.

FIGS. 30-33 illustrate a clamping apparatus 500 in accordance with the present invention that is particularly well suited for blood vessel repair and dural membrane repair. The apparatus 500 includes an inner plate 510, an outer plate 520 and a coupler 530 wherein the apparatus 500 is similar to apparatuses 100 and 200 above, namely that the operational concept behind the apparatus 500 relating to the repair of a defect in dural membrane or vascular wall is to clamp or trap the edges of the defect in the dura or vascular wall using the two plates 510 and 520 secured and biased toward one another which will securely trap the edges of the defect between the plates.

Similar to the embodiment of FIG. 12 described above, each plate 510 and 520 is formed with a coiled rib structure. As noted above the rib may further include a flexible mesh, if desired, however the coiled rib may be constructed to form a sufficiently closed plate in situ so as to avoid the need for an additional membrane. Similar to the embodiment of FIG. 12 above, the first end of the coiled rib forming each plate 510 and 520 is fixedly secured to the coupler 530 at attachment groove 532 with the distal end of the rib extending away in a coiled fashion. Adhesive or other fastening method (e.g. tack welding) may be used to supplement the secure attachment of each rib to the coupler 530.

Specific to the embodiment of FIGS. 30-33, each coiled rib extends from the attachment end to the distal end of the rib in a helical and conically expanding form, as shown in FIGS. 30-32, forming opposed frusto-conical plates 510 and 520. The ribs form the respective opposed matching plates 510 and 520. The coiled structure of the respective ribs provides the biasing clamping force to the apparatus 500. Further the coiled structure for each rib allows for certain advantages in apparatus 500 placement as the coils can be collapsed or contracted to ease in positioning. In this embodiment the outermost or distal segment of the ribs of each plate 510 and 520 will engage the tissue, with this engagement being at least 360 degrees (1 loop) surrounding the defect to secure the tissue around the defect. Several "loops" (or portions thereof) of rib of each plate 510 and 520 may be engaged with the tissue in the final engaged position, as during engagement the base of each frusto conical plate 510 and 520 will be pressed toward the attachment end of the plate bringing more of the distal end of each rib into contact with the clamped tissue. The orientation of the plates 510 and 520 is effectively defined by the plane of the tissue engaging loop(s) or rib portion at the distal end of the plates 510 and 520, and this orientation is substantially perpendicular to the axis of the coupler 530. Thus the perpendicular plate orientation of the apparatus 500 is similar to the plate orientations of apparatuses 100 and 200 discussed above.

Figure 19:
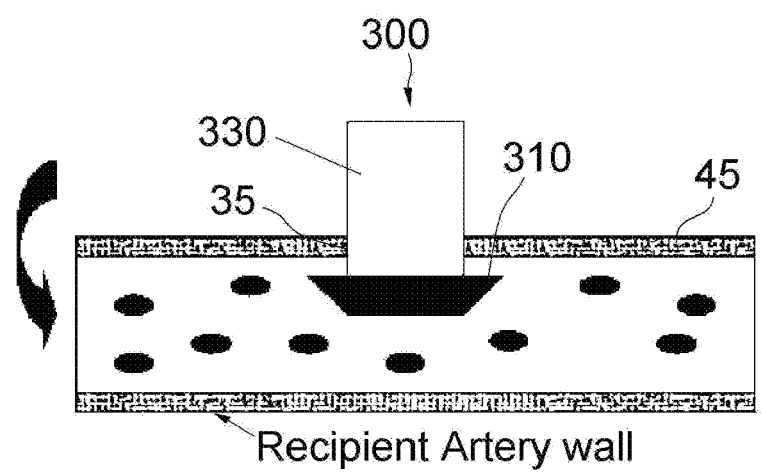
FIGS. 19-20 are schematic views showing the deployment of an inner annular plate for a vascular anastomotic device according to one embodiment of the present invention.
Figure 20:
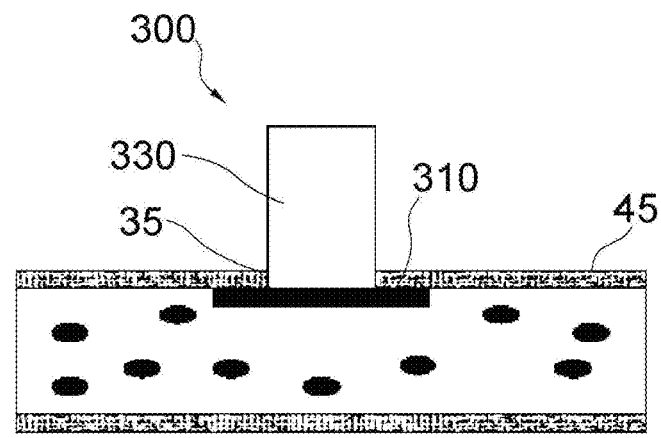

A surgical vascular anastomotic apparatus 300 according a non-limiting embodiment of the present invention includes placing an inner annular plate 310 on an inner surface of the graft receiving vascular wall 45 in a position completely overlapping the bypass opening 35 in the vascular wall. The bypass opening 35 is essentially a planned or inserted "defect" in the vascular wall 45 and thus uses the same reference numeral. The central opening in the annular plate 310 aligns with the bypass opening 35. FIGS. 19-20 are schematic views showing the deployment of the inner annular plate 310 for the vascular anastomotic device 300 according to one embodiment of the present invention. The inner annular plate 310 includes a hollow coupler 330.

Figure 21:
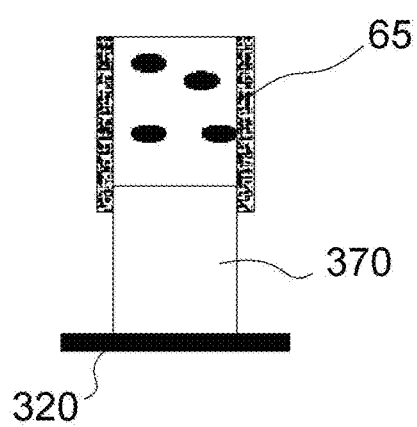
FIGS. 21-22 are schematic views showing the attachment of a vascular bypass graft to an annular outer plate for attachment with the inner annular plate of FIGS. 19-20.
Figure 22:
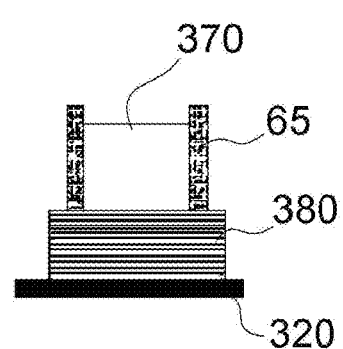

A bypass graft 65 is coupled to an annular outer plate 320 such as shown in FIGS. 21 and 22. The outer plate 320 my include a hollow coupling stem 370 and matching locking ring collar 380 to secure the graft 65 there between, through friction or together with adhesives, or other coupling mechanisms that may be known in the art.

Figure 23:
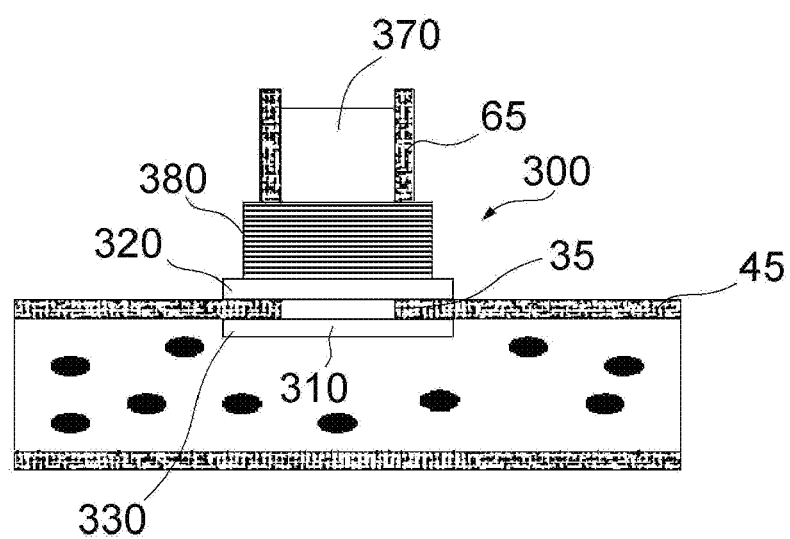
FIG. 23 is a schematic view of the assembled vascular device of FIGS. 19-22.

The annular outer plate 320 is placed on an outer surface of the graft receiving vascular wall 45 in a position completely overlapping the bypass opening 35 in the vascular wall 45 and aligned with the annular inner plate 310. The inner plate 310 is coupled to the outer plate 320 through coupler 330 such that the peripheral edges of the vascular wall 45 around the bypass opening 35 is securely clamped between the inner and outer plates 310 and 320 to provide a watertight coupling (other than through the bypass opening 35 and graft 65) in the vascular wall 45 for the bypass graft 65 attached to the outer annular plate 320. FIG. 23 is a schematic view of the assembled vascular anastomotic assembly 300.

The annular inner plate 310 may be formed in the manner discussed above in connection with the inner plate 110 and is analogous thereto, except for the central hole in the plate 310 allowing flow through the bypass graft 65. The outer plate 320 may be formed in the manner discussed above in connection with the outer plate 120 and is analogous thereto, except for (1) the central hole in the plate 320 allowing flow through the bypass graft 65 and (2) a mechanism to couple the graft 65 thereto. Further, the coupler 330 may be formed in the manner discussed above in connection with the coupler 130 and is analogous thereto, although coupler 330 must allow flow through the bypass graft 65.

It should be apparent that there are many variations to the present invention that can be found within the spirit and scope of the present invention. The key aspects of the surgical method and surgical clamping apparatus of repairing a defect in the dura is (a) placing an inner plate having a perimeter, or plan view, larger than the perimeter of the defect on an inner surface of the defect in the dura in a position completely overlapping the defect in the dura, (b) placing an outer plate having a perimeter, or plan view, larger than the perimeter of the defect on an outer surface of the defect in the dura in a position completely overlapping the defect in the dura and aligned with the inner plate, and (c) coupling the inner plate to the outer plate such that the peripheral edges of the defect in the defect in the dura is securely clamped between the plates to provide a watertight repair to the defect in the dura. Similar methods and apparatus are described for the repair of a defect in the vascular wall and for anastomosis of a body lumen, in particular a vascular anastomosis. The surgical method and surgical clamping apparatus is intended to be defined by the appended claims and equivalents thereto.

What is claimed is:

1. A surgical clamping apparatus for repairing a defect in the dura or blood vessel, said dura clamping apparatus comprising:
   (a) an inner plate configured to be placed on an inner surface of the defect in the dura or blood vessel in a position completely overlapping the defect in the dura or blood vessel, wherein the inner plate has a perimeter in plan view larger than the perimeter in plan view of the defect in the dura or blood vessel, and wherein the inner plate includes at least one radial extending rib in the form of a coil;
   (b) an outer plate configured to be placed on an outer surface of the defect in the dura or blood vessel in a position completely overlapping the defect in the dura or blood vessel and aligned with the inner plate, wherein the outer plate has a perimeter in plan view larger than the perimeter in plan view of the defect in the dura or blood vessel, and wherein the outer plate includes at least one radial extending rib in the form of a coil; and
   (c) a rigid coupling member for coupling the inner plate to the outer plate such that the peripheral edges of the defect in the dura or blood vessel is securely clamped between the inner and outer plates to provide a watertight repair to the defect in the dura or blood vessel, wherein the coupling member is in the form of a guide stem and wherein each coiled rib has an attachment end fixedly secured to the guide stem, wherein the coupling member includes a guide stem extending from the inner plate to the outer plate with an attachment groove for attaching each rib, and wherein a distal segment of the ribs of each plate engage the tissue, with this engagement being at least 360 degrees surrounding the defect to secure the tissue around the defect between the plates and wherein each rib extends helically and conically expanding along the guide stem toward the opposed plate, and wherein the guide stem is maintained along an axial axis centered within the conically expanding ribs.

2. The surgical dura clamping apparatus of claim 1 wherein the inner and outer plates are circular in plan view.

3. The surgical dura clamping apparatus of claim 1 wherein the inner and outer plates are circular in plan view and the outer plate has a larger diameter than the inner plate.

4. The surgical dura clamping apparatus of claim 1 wherein the coupling member includes an adhesive.

5. The surgical dura clamping apparatus of claim 1 wherein the plates are formed of bio-absorbable material.

6. The surgical dura clamping apparatus of claim 1 wherein the inner plate is moveable at least between a retracted position for insertion of the inner plate through the defect and an open fully deployed position.

7. The surgical dura clamping apparatus of claim 6 wherein the direction of movement of the inner plate from the retracted to the open position is in a direction tending to sweep tissue away from the dura or blood vessel defect.

8. A surgical clamping apparatus for repairing a defect in the dura or blood vessel, said dura clamping apparatus comprising:
   (a) an inner plate configured to be placed on an inner surface of the defect in the dura or blood vessel in a position completely overlapping the defect in the dura or blood vessel, wherein the inner plate has a perimeter in plan view larger than the perimeter in plan view of the defect in the dura or blood vessel, and wherein the inner plate includes at a plurality of radial extending ribs in the form of a coil;
   (b) an outer plate configured to be placed on an outer surface of the defect in the dura or blood vessel in a position completely overlapping the defect in the dura or blood vessel and aligned with the inner plate, wherein the outer plate has a perimeter in plan view larger than the perimeter in plan view of the defect in the dura or blood vessel; and
   (c) a rigid coupling member for coupling the inner plate to the outer plate such that the peripheral edges of the defect in the dura or blood vessel is securely clamped between the inner and outer plates to provide a watertight repair to the defect in the dura or blood vessel, wherein the coupling member is in the form of a guide stem and wherein each coiled rib has an attachment end fixedly secured to the guide stem, wherein the coupling member includes a guide stem extending from the inner plate to the outer plate with an attachment groove for attaching each rib, and wherein a distal segment of the ribs of each plate engage the tissue, with this engagement being at least 360 degrees surrounding the defect to secure the tissue around the defect between the plates and wherein each rib extends helically and conically expanding along the guide stem toward the opposed plate, and wherein the guide stem is maintained along an axial axis centered within the conically expanding ribs.

9. A surgical method of repairing a defect in the dura or blood vessel comprising the steps of:
   (a) placing an inner plate on an inner surface of the defect in the dura or blood vessel in a position completely overlapping the defect in the dura or blood vessel, wherein the inner plate includes at least one radial extending rib in the form of a coil and wherein the inner plate has a perimeter in plan view larger than the perimeter in plan view of the defect in the dura or blood vessel;
   (b) placing an outer plate on an outer surface of the defect in the dura or blood vessel in a position completely overlapping the defect in the dura or blood vessel and aligned with the inner plate, whereby the outer plate includes a radial extending rib in the form of a coil and wherein the outer plate has a perimeter in plan view larger than the perimeter in plan view of the defect in the dura or blood vessel; and
   (c) coupling the inner plate to the outer plate such that the peripheral edges of the defect in the dura or blood vessel is securely clamped between the inner and outer plates to provide a watertight repair to the defect in the dura or blood vessel, wherein the coupling includes providing that each coiled rib has an attachment end secured to an axially extending rigid guide stem and each rib extends helically and conically expanding along the guide stem toward the opposed plate, wherein the coupling of the inner plate to the outer plate uses the guide stem extending from the inner plate to the outer plate, with a groove in the guide stem at each end to secure the rib to the stem, and wherein a distal segment of the ribs of each plate engage the tissue, with this engagement being at least 360 degrees surrounding the defect to secure the tissue around the defect between the plates, and wherein each rib extends helically and conically expanding along the guide stem toward the opposed plate, and wherein the guide stem is maintained along an axial axis centered within the conically expanding ribs.

10. The method of claim 9 wherein the inner and outer plates are circular in plan view and wherein the inner plate further includes a flexible webbing.

11. The method of claim 9 wherein the defect is in a blood vessel and the clamping apparatus is configured for use on a defect in a blood vessel.

12. The method of claim 9 wherein the guide stem is substantially perpendicular to the plane of engagement of each plate with the tissue.

13. The method of claim 9 wherein the plates are formed of bio-absorbable material.

14. The method of claim 9 wherein the step of placing an inner plate on an inner surface of the defect comprises the steps of inserting the inner plate in a retracted position through the defect and then opening the inner plate to a fully deployed position.

15. The method of claim 14 wherein the opening of the inner plate is in a direction tending to move tissue away from the area of the tissue having the defect.

16. The method of claim 9 wherein the defect is in the dural tube within the spinal column.

* * * * *